United States Patent [19]
Bhutani

[11] 3,993,693
[45] Nov. 23, 1976

[54] METHOD FOR PRODUCING PERCHLOROMETHYL MERCAPTAN

[75] Inventor: Sudhir K. Bhutani, Orange, Conn.

[73] Assignee: Olin Corporation, New Haven, Conn.

[22] Filed: July 30, 1975

[21] Appl. No.: 600,749

[52] U.S. Cl. ............................................. 260/543 H
[51] Int. Cl.$^2$ .......................................... C07C 149/16
[58] Field of Search ................................ 260/543 H

[56] References Cited
UNITED STATES PATENTS

| | | | |
|---|---|---|---|
| 2,545,285 | 3/1951 | Kamlet | 260/543 H |
| 2,575,290 | 11/1951 | Ohsol et al. | 260/543 H |
| 2,647,143 | 7/1953 | Pitt et al. | 260/543 H |
| 2,759,969 | 8/1956 | Jonas | 260/543 H |
| 3,014,071 | 12/1961 | Hoyt et al. | 260/543 H |
| 3,544,625 | 12/1970 | Masat et al. | 260/543 H |
| 3,673,246 | 6/1972 | Meyer et al. | 260/543 H |
| 3,808,270 | 4/1974 | Rupp et al. | 260/543 H |
| 3,865,553 | 2/1975 | Masat et al. | 260/543 H |

*Primary Examiner*—Norman Morgenstern
*Attorney, Agent, or Firm*—F. A. Iskander; T. P. O'Day

[57] ABSTRACT

An improved process is disclosed for the manufacture of perchloromethyl mercaptan by chlorination of carbon disulfide in the presence of aqueous hydrochloric and sulfuric acids in which a high concentration of sulfuric acid is maintained in the reactor to obtain an aqueous by-product acid mixture from which sulfuric and hydrochloric acids may be separated by a simple distillation to give commercial grade hydrochloric acid and sulfuric acid.

4 Claims, 1 Drawing Figure

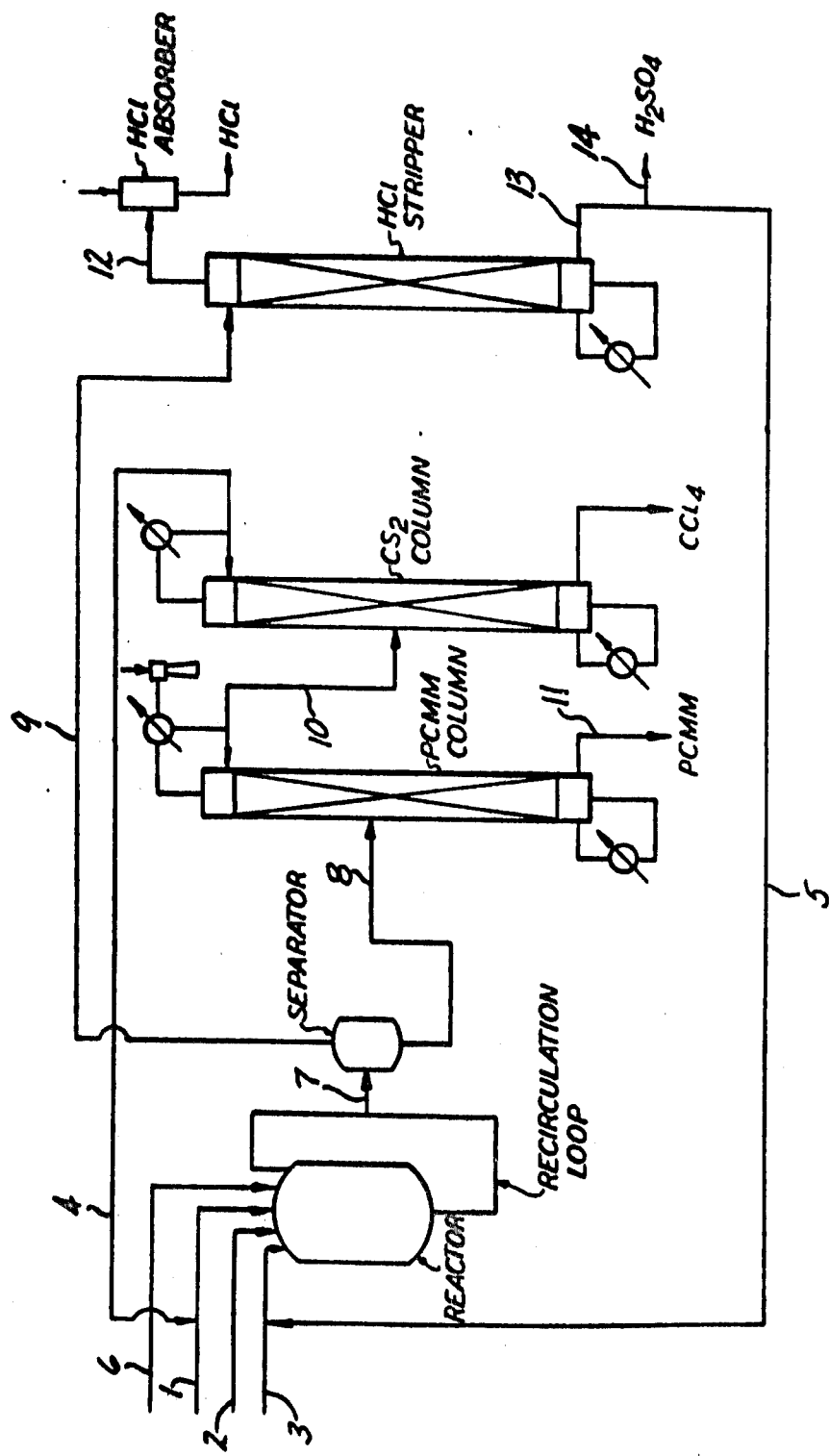

METHOD FOR PRODUCING PERCHLOROMETHYL MERCAPTAN

BACKGROUND OF THE INVENTION

1. Field of Invention

The present process relates to a process for producing perchloromethyl mercaptan by chlorination of carbon disulfide in the presence of aqueous hydrochloric acid. More particularly, the invention comprises chlorinating carbon disulfide in the presence of 5–38% hydrochloric acid in the presence of high concentrations of sulfuric acid, enabling one to more effectively utilize by-products of the reaction and to thereby increase the economics of prior processes. Specifically, aqueous sulfuric acid replaces water as a feed to the reactor in order to facilitate recovery of hydrochloric and sulfuric acids.

2. Prior Art

The preparation of perchloromethyl mercaptan (PCMM), also known as trichlormethane sulfenyl chloride, by chlorinating carbon disulfide is well known to those skilled in the art. Since first proposed by Rathke [Ber. 3,859 (1870)] much attention has been devoted to the purification and isolation of perchlormethyl mercaptan and to improving yields thereof. Perhaps the most significant problem was to find a method for inexpensively producing a product which is substantially free of sulfur chlorides and in particular sulfur monochloride, which has a boiling point very close to that of perchloromethyl mercaptan. Numerous multistep processes were proposed for removing sulfur chlorides as shown in U.S. Pat. Nos. 2,664,442; 2,666,081 and 2,647,143. A process for simultaneously producing perchloromethyl mercaptan substantially free of sulfur chlorides was described in Masat et al, U.S. Pat. No. 3,544,625 wherein it was disclosed that the sulfur chlorides could be decomposed to hydrochloric and sulfuric acids during chlorination of carbon disulfide if the chlorination were conducted on a mixture of carbon disulfide and an aqueous solution of hydrochloric acid. The only sulfuric acid occurring in the process was that generated by the reaction itself.

While the Masat el al process represents an advantageous method for producing perchloromethyl mercaptan which is substantially free of sulfur chlorides, it has one serious disadvantage. It produces a by-product acid mix containing from about 10–15% sulfuric acid and generally from about 20% to about 35% hydrochloric, balance mostly water. This by-product mix must be disposed of or utilized economically if the process is to be economical as well practicable from an effluent pollution standpoint. As the process was heretofore practiced, the by-product mix is either disposed of as such or neutralized and disposed of. This is wasteful and expensive. It has also been proposed to use the by-product mix as neutralization acid, but this again represents an uneconomical use and one for which there is frequently no demand.

A much more desirable solution would be to conduct the chlorination in a manner which would permit one to recover commercial grade hydrochloric acid from the by-product mix. The recommended means for accomplishing this to date is by utilizing submerged combustion of the by-product mix and this is so expensive in terms of energy requirements that it is for all practical purposes commercially unacceptable.

The difficulty in separating the respective acids from the by-product mix arises by virtue of the fact that hydrochloric acid and water form a maximum boiling azeotrope of about 20 wt. % HCl at atmospheric pressure. Distillation of a hydrochloric acid solution of less than azeotropic concentration produces hydrochloric acid having an acid concentration no greater than the azeotrope concentration. Conversely distillation of a hydrochloric acid solution of greater than azeotropic concentration enables one to remove as commercial grade hydrochloric acid only that amount which is in excess of the azeotropic concentration. The balance stays behind as the azeotrope is distilled off as such.

It has now been found that if chlorination may be conducted in the presence of high concentrations of sulfuric acid, preferably recycled from the process, one may substantially increase the quantity of high quality hydrochloric acid which may be recovered from the aqueous by-product stream by a simple distillation. If the chlorination is conducted in the presence of sufficient sulfuric acid to produce an aqueous by-product phase having a sulfuric acid concentration of 38% or greater, the excess sulfuric acid may be similarly recovered substantially free of hydrochloric acid.

In the following description and claims, all percentages are given on a weight basis unless it is expressly stated otherwise.

SUMMARY OF THE INVENTION

In accordance with the present invention perchloromethyl mercaptan is produced by chlorinating a well agitated mixture of carbon disulfide and an aqueous solution comprising 5–38% hydrochloric acid in the presence of sufficient sulfuric acid to dissolve said hydrochloric acid and to produce an aqueous by-product phase comprising from 20% to about 55% sulfuric acid.

The reaction mixture is separated into an aqueous and organic phases, perchloromethyl mercaptan recovered from the organic phase, the aqueous phase distilled to recover hydrochloric acid overhead and a bottoms product comprising an aqueous solution of sulfuric acid, and a major portion of the bottoms product is recycled to the reaction step.

DETAILED DESCRIPTION

Referring now to the accompanying drawing, there is shown a schematic flow diagram showing the flow of materials in accordance with the preferred embodiment of the present invention.

The basic reaction of the present invention may be represented by the reaction

$$CS_2 + 5Cl_2 \xrightarrow[H_2SO_4]{HCl} Cl_3CSCl + H_2SO_4 + 6HCl$$

In accordance therewith chlorine is passed through a reaction mixture containing carbon disulfide, hydrochloric acid, sulfuric acid and water and the sulfuric acid content thereof is maintained at a level sufficient to produce a reaction product having an aqueous by-product phase containing from about 20% to about 55% sulfuric acid, advantageously 30–50% and preferably 38% to about 45%.

The sulfuric acid content of the reaction mixture and ultimately of the aqueous by-product phase represents the sum of that added via line 3 and/or 5 and that produced during the reaction itself by the hydrolysis of sulfur chlorides to hydrochloric acid and sulfuric acid, the latter being about 1 mole per mole of carbon disulfide reacted. In prior processes utilizing aqueous hydrochloric acid, sulfuric acid was also present but at very low concentrations, specifically concentrations producing an aqueous by-product phase having from about 8% to about 13% sulfuric acid. In the present invention sulfuric acid is substituted for water as a solvent for hydrochloric acid and is thus utilized in concentrations not heretofore contemplated by those skilled in the art.

As shown in the drawing, carbon disulfide is added to a suitable reaction via line 1 and may be mixed with recycle carbon disulfide entering via line 4. Gaseous chlorine is added via line 2 and aqueous sulfuric acid is supplied via line 3 which may contain or consist of recycle acid from the bottom of hydrochloric acid stripper.

The quantity of hydrochloric acid present in the reactor during operation results both from the reaction itself and from acid which may be added, for example, via line 6 or if desired as recycle acid present in sulfuric acid recycle, line 3. Most of the hydrochloric acid necessary for operating on a continuous basis will be generated by the reaction itself so that it is usually necessary to add additional hydrochloric acid only during startup. The amount of hydrochloric acid required is from 5-38% of the total reaction mixture and preferably from 10% to about 30% of the reaction mixture. The present invention, therefore, utilizes the teaching of U.S. Pat. No. 3,544,625 insofar as it relates to hydrochloric acid and to that extent the teaching thereof is hereby incorporated herein by reference.

As shown in the drawing, the product overflows the reactor, a portion thereof flows via line 7 into a separator from which the lower organic phase is removed via line 8 and the upper aqueous phase comprising the by-product acid mix is removed via line 9. The remainder is cooled and recirculated to the reactor.

The organic phase is then suitably sent to a distillation column where low boiling carbon disulfide and carbon tetrachloride are taken overhead via line 10 and perchloromethyl mercaptan (PCMM) is removed via line 11 as the bottoms product. The low boiling overheads are sent via line 10 to a second column where carbon disulfide is distilled overhead and recycled via line 4 to the reactor.

The aqueous by-product phase removed from separator via line 9 is sent to an hydrochloric acid recovery column or stripper where hydrochloric acid of any desired concentration is distilled overhead via line 12. If necessary, the recovered hydrochloric acid can be further purified, for example, by passing through an adiabatic absorber and/or a carbon bed to produce commerical grade muriatic acid.

The quality of the sulfuric acid recovered as a bottoms product from stripper via line 13 will depend on the sulfuric acid content of the aqueous by-product phase in line 9 in addition to the usual factors which effect completeness of separation such as temperature, number and efficiency of plates, etc.

If, as in the preferred embodiment, the aqueous phase has an acid concentration of above about 38%, that is, at or above the concentration which will effectively break the water/hydrochloric acid azeotrope, substantially all hydrochloric acid is readily recovered by a simple atmospheric pressure distillation and the bottoms product exiting from stripper will be a solution of sulfuric acid which is substantially free of hydrochloric acid. As shown in the drawing, a major portion of this, for example, in the range of 60-95% of the product sulfuric acid is recycled to the reactor, the balance being purged via line 14 and concentrated to convert it to commercial grade sulfuric acid.

If the aqueous by-product phase has a sulfuric acid content below about 38%, i.e., below the amount needed to effectively break the hydrochloric acid/water azeotrope, the amount of hydrochloric acid recoverable per pass is reduced and the amount present in the by-product sulfuric acid is increased proportionately, making the latter unsuitable for sale as commercial grade sulfuric acid. Nevertheless, the major portion may advantageously be recycled to the reactor with only a minor portion being discarded or used as neutralization acid. In recycling the sulfuric acid may be diluted as desired with water.

The chlorination step is suitably carried out over a wide temperature range anywhere between about 0° C. and about 45° C., preferably in the range of 20° C. to 35° C.

The reaction may be conducted as a batch or continuous reaction, but the continuous process is preferable. In conducting the reaction, the reaction mixture should be rapidly agitated to assure adequate contact between the imiscible reaction components. This can be accomplished utilizing mechanical agitators or mixers, by vibration or any other known mechanical means or by utilizing reaction devices which provide sufficient agitating contact between the various components. The reactor itself may be, for example, a drum reactor provided with suitable agitators, or alternatively, a tower type reactor such as that set forth in U.S. Pat. No. 3,865,553.

The initial chlorination is retarded by the presence of oxygen. It is thus preferred that a closed reactor be utilized and that the reactor vapor space be purged, for example, with chlorine, before agitation is commenced.

EXAMPLE I

Sulfuric Acid Feed

Carbon disulfide, chlorine and 40% sulfuric acid were fed to a continuous stirred tank reactor operated at 30° C. Feed ratios (by weight) were 1.00:3.76:13.47, respectively. Residence time in the reactor was 3.5 hrs. The organic phase was separated from the aqueous phase and analyzed 80.6% perchloromethyl mercaptan, 11.1% carbon disulfide, 7.6% carbon tetrachloride giving a 78.4% yield of perchloromethyl mercaptan for a carbon disulfide conversion of 79.7%. The aqueous phase analyzed 40.6% $H_2SO_4$ and 13.2% hydrochloric acid. This acid was distilled in a packed column to give an overhead product analyzing 96.3% HCl, 3.7% $H_2O$. The bottoms product of the column analyzed 47.0% $H_2SO_4$, 0.6% HCl indicating substantially all HCl had been recovered overhead.

EXAMPLE II

Water Feed

Carbon disulfide, chlorine and water were fed to a continuous reactor operated at 30° C. in weight ratios of 1.00:4.05:6.32, respectively. Residence time was 2.5 hrs. After phase separation, the organic phase analyzed 80.2% perchloromethyl mercaptan, 8.0% carbon disulfide, 10.1% carbon tetrachloride and 1.3% $SCl_2$. The yield of PCMM was 82.6% for an 83% $CS_2$ conversion.

The aqueous phase analyzed 28.7% HCl, 12.8% H$_2$SO$_4$. Distillation of the aqueous phase produces a small amount of HCl overhead, the balance remaining in the sulfuric acid bottoms product. HCl is thus lost and the sulfuric acid is not suitable for recycle or for conversion to commercial grade sulfuric acid.

What is claimed is:

1. In a process for preparing perchloromethyl mercaptan wherein chlorine is passed through a reaction mixture of carbon disulfide and an aqueous solution comprising 5–38% by weight hydrochloric acid with agitation, the improvement which comprises:
   a. Adding to said mixture sufficient sulfuric acid to produce a reaction product having an aqueous phase consisting essentially of said concentration of hydrochloric acid and from about 20% to about 55% sulfuric acid,
   b. separating said aqueous phase from an organic phase consisting essentially of perchloromethyl mercaptan,
   c. removing hydrochloric acid from said aqueous phase and
   d. recycling a major portion of the resulting solution of sulfuric acid to said mixture.

2. The process of claim 1 wherein said aqueous phase comprises from about 30% to about 50% sulfuric acid.

3. The process of claim 2 wherein said aqueous phase is distilled, said hydrochloric acid removed overhead and aqueous sulfuric acid recovered as a bottoms product.

4. The process of claim 3 wherein said aqueous phase comprises 38–45% sulfuric acid, wherein substantially all said hydrochloric acid is removed overhead and said bottoms product is a solution of sulfuric acid substantially free of hydrochloric acid.

* * * * *